(12) United States Patent
Hisada et al.

(10) Patent No.: US 8,095,321 B2
(45) Date of Patent: Jan. 10, 2012

(54) MODELING DEVICE, PROGRAM, COMPUTER-READABLE RECORDING MEDIUM, AND METHOD OF ESTABLISHING CORRESPONDENCE

(75) Inventors: Toshiaki Hisada, Tokyo (JP); Hiroshi Kurokawa, Tokyo (JP); Nobuhiko Oshida, Tokyo (JP); Masafumi Yamamoto, Tokyo (JP); Takumi Washio, Tsukuba (JP); Jun-ichi Okada, Kashiwa (JP); Hiroshi Watanabe, Tokyo (JP); Seiryo Sugiura, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 1078 days.

(21) Appl. No.: 11/795,888

(22) PCT Filed: Jan. 25, 2006

(86) PCT No.: PCT/JP2006/301142
§ 371 (c)(1),
(2), (4) Date: Jul. 24, 2007

(87) PCT Pub. No.: WO2006/080349
PCT Pub. Date: Aug. 3, 2006

(65) Prior Publication Data
US 2008/0120078 A1     May 22, 2008

(30) Foreign Application Priority Data

Jan. 26, 2005   (JP) ................................. 2005-018949

(51) Int. Cl.
*G01N 33/48* (2006.01)
*G01N 33/50* (2006.01)
*G06F 17/50* (2006.01)
*G06F 7/60* (2006.01)

(52) U.S. Cl. .................................. 702/19; 703/2; 703/1
(58) Field of Classification Search ........................ None
See application file for complete search history.

(56) References Cited

U.S. PATENT DOCUMENTS 5,273,038 A * 12/1993 Beavin ........................... 600/416
5,947,899 A * 9/1999 Winslow et al. ............... 600/410

FOREIGN PATENT DOCUMENTS

| JP | 62-217936 | 9/1987 |
| JP | 64-049540 | 2/1989 |
| JP | 06-063026 | 3/1994 |
| JP | 2001-061789 | 3/2001 |
| JP | 2002-051998 | 2/2002 |
| JP | 2002-537008 | 11/2002 |
| WO | WO 00/46689 | 8/2000 |

OTHER PUBLICATIONS

Carey Stevens et al. "Sarcomere length changes in a 3D mathematical model of the pig ventricles", Progress in Biophysics &Molecular Biology 82(2003), p. 229-241.
Carey Stevens et al. "Ventricular mechanics in diastole: material parameter sensitivity", Journal of Biomechanics 36(2003), p. 737-748.
D.F. Scollan et al., "Histological validation of myocardial microstructure obtained from diffusion tensor magnetic resonance imaging" Histological validation of myocardial structure from MRI, 1998 p. H2308-H2318.
D.F. Scollan et al.,"Reconstruction of cardiac ventricular geometry and fiber orientation using magnetic resonance imaging" Annals of Biomedical Engineering, vol. 28, p. 934-944, 2000.

\* cited by examiner

*Primary Examiner* — Jason Sims
(74) *Attorney, Agent, or Firm* — Harness, Dickey & Pierce, P.L.C.

(57) ABSTRACT

A modeling device is disclosed that easily projects characteristic information obtained from an object onto a differently-shaped object, even if the object, from which the characteristic information is obtained, has a complex shape. A modeling device in one embodiment of the present invention includes a virtually electrifying section to calculate an electric potential at a spot in a heart at the time when a predetermined voltage is applied to the heart, and a projecting section to project a fiber orientation onto a heart model created on the basis of shape information that is input to the input section. The projecting section specifies a spot to be a target of projection on the basis of the electric potential obtained by the virtually electrifying section. Use of the electric potential in specifying the spot makes it possible to easily project the fiber orientation onto any heart having complex and various shapes.

6 Claims, 9 Drawing Sheets

MODELING DEVICE, PROGRAM, COMPUTER-READABLE RECORDING MEDIUM, AND METHOD OF ESTABLISHING CORRESPONDENCE

TECHNICAL FIELD

The present invention relates to a modeling device, a program, and a computer-readable recording medium, and particularly, relates to a modeling device virtually forming an object model, a program used in the modeling device, and a computer-readable recording medium storing the program. The present invention also relates to a method of establishing a correspondence between an object and another object.

BACKGROUND ART

A heart contracts and relaxes, that is to say, beats at a regular rhythm. Arrythmia is a serious disease that a period of this cardiac beat becomes irregular, sometimes causing cardiac arrest. Various and detailed studies have been carried out on the cardiac beat mechanism for medical treatment and diagnosis of arrythmia.

Cardiac contraction occurs as follows. First, electrical impulses are emitted at a constant period from a part of a right atrium, which part is called a sinoatrial node. The electrical impulses are passed to cardiac muscle cells of the right atrium and cardiac muscle cells of a left atrium. Consequently, myofibrils in the cardiac muscle cells contract. When this contraction of the myofibrils occurs all over the right atrium and the left atrium, the right atrium and the left atrium are caused to contract. Further, a part of the electrical impulses reaches an atrioventicular node located below the right atrium and in the vicinity of an interventricular septum. After reaching the atrioventicular node, the impulses pass through His bundles, right and left bundle branches, and Purkinje fibers, and then reach a left ventricle and a right ventricle, causing the left ventricle and the right ventricle to contract. As the foregoing discusses, a cardiac beat is caused by electrical impulses passing through the heart.

The cardiac muscle cells are in the shape of a cylinder with a diameter of approximately 5 to 20 μm and a length of approximately 100 μm. The cardiac muscle cells are arranged in a certain orientation to form a bundle. An orientation of the length of the cardiac muscle cells is same as that of the myofibrils in the cells, and therefore is called a fiber orientation. Muscle contraction is caused by sliding movement of the myofibrils. The fiber orientation is closely related to cardiac contraction movement. Therefore, the fiber orientation is an important factor in mechanically analyzing the cardiac contraction. Further, an electric current passes easily in the fiber orientation in the cells. The fiber orientation relates to a conduction orientation of the electrical impulses in the heart. Therefore, the fiber orientation is an important factor also in analyzing conduction pathways of the electrical impulses in the heart.

It is empirically known that appropriate fiber placement is important for efficient cardiac contraction and blood pulsation. The fiber orientation varies in different parts. The fiber orientations of the entire heart are complex. Conventionally, the fiber orientation is measured by anatomical and histological methods. In view of ethics, a heart of a dog or a pig, which are relatively close to a human, is utilized in place of a human heart.

For example in Documents 1, 2, the fiber orientation and the sheet orientation of a pig heart are measured, and this measured fiber orientation data is organized with introduction of three coordinate systems, such as an ellipse coordinate system, and Hermitian finite element. The sheet orientation is in connection with a plane (sheet) where the cardiac muscle cells are arranged. Mathematically, the sheet orientation is vertical to the plane.

Documents 3 and 4 disclose a method of measuring and calculating a fiber orientation with the use of diffusion tensor magnetic resonance imaging (MRI). A spatial distribution of the fiber orientation of a dog heart is actually obtained, and is compared with histological data for verification.

The foregoing results of measurement have roughly clarified a pattern of the fiber placement in the heart. Findings from animals are utilized to creates a virtual human heart model in a calculator, and attempts to contribute to medical care and drug discovery have been made by simulations and the like.

However, no modeling device has been realized by which information on the fiber orientation of the cardiac muscle cells, which information is obtained from an animal, is buried in a human heart to perform modeling suitably. This is due to the following reasons.

First, no coordinate system suitable to specify the spots in a heart has not been found. For example, to apply a fiber orientation obtained from animal onto a human heart model, it is necessary to establish a one-by-one correspondence between a spot in the animal heart and a spot in the human heart. However, the shapes of the hearts vary among species, and further, among individuals. Furthermore, the shapes of the hearts are very complex. Therefore, it is extremely difficult with an ordinary XYZ-axes orthogonal coordinate system or the like to set a correspondence between spots of two different hearts. In view of the foregoing circumstances, there have been demands for a modeling device by which characteristic information, such as a fiber orientation, obtained from an object is easily projected onto a differently-shaped object, even if the shape of the object, from which the characteristic information is obtained, is complex, such as the shape of a heart.

Further, no method of suitably setting a local coordinate system to define the fiber orientation and the like at a spot in a heart has been found. The fiber orientation, for instance, is closely related to the outer shape of the heart. For example, the fiber orientation at a point on a surface of the epicardium of the heart is included within a plane that is in contact with the point. However, if the fiber orientation information is expressed with the use of an ordinary global coordinate system, it is not possible to express the fiber orientation in such a way as to correspond to the outer shape of the heart, because the global coordinate system has no relationship with the outer shape of the heart. Therefore, if the fiber orientation data obtained from animals is directly applied to the human heart, contradiction may arise in the fiber orientation. For example, the fiber orientation protrudes from the epicardium of the heart. Further, even if a hypothesis about the fiber orientation on the basis of the findings obtained from the animal heart is to be applied, it is not possible to apply the hypothesis naturally. In view of the foregoing reasons, the local coordinate system needs to be set at respective spots in the heart. The heart, however, has a very complex shape. Setting the local coordinate system by performing a geometric calculation each time on the basis of the shape of the heart requires a vast amount of calculation and is therefore not realistic. In view of the foregoing circumstances, there have been demands for a modeling device by which orientation characteristic information, such as a fiber orientation, that is related to an outer shape of a heart is easily projected from an object onto another object.

(Document 1)

Stevens C, Hunter P J. Sarcomere length changes in a 3D mathematical model of the pig ventricles. Prog Biophys Mol Biol. 2003 May-July; 82(1-3): 229-241.

(Document 2)

Stevens C, Remme E, LeGrice I, Hunter P. Ventricular mechanics in diastole: material parameter sensitivity. J Biomech. 2003 May; 36(5): 737-748.

(Document 3)

Scollan D F, Holmes A, Winslow R, Forder J. Histological validation of myocardial microstructure obtained from diffusion tensor magnetic resonance imaging. Am J Physiol. 1998 December; 275(6 Pt 2): H2308-H2318.

(Document 4) Scollan D F, Holmes A, Zhang J, Winslow R L. Reconstruction of cardiac ventricular geometry and fiber orientation using magnetic resonance imaging. Ann Biomed Eng. 2000 August; 28(8): 934-944.

DISCLOSURE OF INVENTION

The present invention is in view of the foregoing problems, and has as a main object to realize a modeling device by which characteristic information obtained from an object is easily projected onto a differently-shaped object, even if the object, from which the characteristic information is obtained, has a complex shape.

Another object of the present invention is to realize a modeling device by which orientation characteristic information is easily projected from an object onto another object, which information is related to the shape of the object.

To solve the above problems, a modeling device of the present invention is adapted so that the modeling device includes: a first input section to which shape information on an object is input; a second input section to which characteristic information is input, the characteristic information indicating a correspondence between a spot in the object and a characteristic; virtually electrifying means for obtaining by calculation, on a basis of the shape information that is input to the first input section, an electric potential at a spot in the object at a time when a predetermined voltage is applied to the object; and projecting means for projecting, onto an object model based on the shape information that is input to the first input section, the characteristic contained in the characteristic information that is input to the second input section, the projecting means specifying a spot in the object model on a basis of the electric potential obtained by the virtually electrifying means, onto which spot the characteristic is to be projected.

The characteristic information that is input to the second input section contains a correspondence between the spot in the object and the characteristic. The projecting means projects the characteristic information onto the object model that is input to the first input section. Thus, the characteristic corresponding to the spot is projected onto the object model. The "spot" may be either of a point and an area.

A spot in the object is specified on the basis of the electric potential obtained by the virtually electrifying means. The virtually electrifying means virtually applies the predetermined voltage. Therefore, the electric potential at a spot in the object is in the range of 0V to the predetermined voltage. Accordingly, a spot in the object is specified in the range of 0V to the predetermined voltage. This makes it possible to specify the spot in various objects having different shapes by use of a common scale (not smaller than 0V and not greater than the predetermined voltage). Accordingly, for example a function with a variable of a coordinate based on the electric potential is input to the second input section as the characteristic information, the characteristic is easily projected regardless of shape of a target object. In other words, with the modeling device of the present invention, the characteristic is projected onto various objects having different shapes. Further, no geometric calculation is necessary to specify the spot, so that the characteristic is easily projected onto an object even if the object has a complex shape.

To solve the above problems, a different modeling device of the present invention is adapted so that the modeling device includes: a first input section to which shape information on a first object is input; a second input section to which characteristic information is input, the characteristic information containing a spot in the second object and a characteristic at the spot; a third input section to which shape information on the second object is input; virtually electrifying means for obtaining by calculation, on a basis of the shape information that is input to the first input section and the shape information that is input to the third input section, (i) an electric potential at a spot in the first object at a time when a predetermined voltage is applied to the first object and (ii) an electric potential at a spot in the second object at a time when the predetermined voltage is applied to the second object; and projecting means for: specifying, on a basis of the electric potential obtained by the virtually electrifying means, a spot in the first object model based on the shape information that is input to the first input section, the spot in the first object model corresponding to the spot in the second object, and the spot in the second object being contained in the characteristic information that is input to the second input section; and projecting the characteristic onto the spot.

With this configuration, the virtually electrifying means applies the voltage to obtain the electric potential at a spot in the first object. In the same manner, the virtually electrifying means obtains the electric potential at a spot in the second object. Then, the projecting means establishes a correspondence between the spot in the second object and the spot in the first object model on the basis of the electric potential at the spot in the second object. For example, the projecting means establishes a correspondence between the spot in the second object and the spot, having a same electric potential as that of the spot in the second object, in the first object model. Thereafter, the projecting means projects the characteristic information on the spot in the second object, which characteristic information is input to the second input section, onto the corresponding spot in the first object model. By the foregoing way, the characteristic information on a spot in the second object is projected onto the corresponding spot in the first object.

The projecting means establishes the correspondence between the spot in the first object and the spot in the second object on the basis of the electric potential obtained by the virtually electrifying means. The virtually electrifying means applies the predetermined voltage. Therefore, the electric potential at a spot in the objects is in the range of 0V to the predetermined voltage. Accordingly, a spot in each of the objects is specified in the range of 0V to the predetermined voltage. This makes it possible to easily establish a correspondence by use of a common scale (not smaller than 0V and not greater than the predetermined voltage) even if the shape of the first object and the shape of the second object are complex and different. Accordingly, with the modeling device of the present invention, characteristic information obtained from an object is easily projected onto a differently-shaped object, even if the object, from which the characteristic information is obtained, has a complex shape. Further, no geometric calculation is necessary to establish a correspondence between spots, so that the characteristic is easily projected even if the shape of the object is complex.

Respective means of the modeling device may be realized by hardware, or may be realized by causing a computer to execute a program. Specifically, a program of the present invention causes a computer to operate as the respective means of any one of the modeling devices described above. Further, a recording medium of the present invention stores the program.

Executing the program, the computer operates as the respective means of the modeling device. This realizes a modeling device by which characteristic information obtained from an object is easily projected onto a differently-shaped object, even if the object, from which the characteristic information is obtained, has a complex shape.

To solve the above problems, a method of establishing a correspondence according to the present invention is adapted so that the method includes: obtaining (i) an electric potential distribution at a time when a predetermined voltage is applied to the first object and (ii) an electric potential distribution at a time when the predetermined voltage is applied to the second object; and establishing, on a basis of the electric potential distribution obtained, the correspondence between the spot in the first object and the spot in the second object.

With this arrangement, the correspondence between the points or areas in the objects is established on the basis of the electric potential distribution. The electric potential distribution is a distribution at a time when the predetermined voltage is applied. Therefore, any spot in the objects is in the range of 0V to the predetermined voltage. Accordingly, any spot in the objects is specified in the range of 0V to the predetermined voltage. The foregoing arrangement makes it possible to establish a correspondence between the points or areas by use of a common scale (not smaller than 0V and not greater than predetermined voltage), even if the shapes of the first object and the second object are different.

Additional objects, features, and strengths of the present invention will be made clear by the description below. Further, the advantages of the present invention will be evident from the following explanation in reference to the drawings.

BEST MODE FOR CARRYING OUT THE INVENTION

Embodiment 1

The following describes an embodiment of the present invention, with reference to FIGS. 1 to 8. In the present embodiment, an exemplary case is discussed in which an object is a human heart, and a characteristic employed is a characteristic regarding a fiber orientation of cardiac muscle cells. Specifically, a modeling device that suitably projects a hypothesis regarding the fiber orientation of the cardiac muscle cells onto a human heart model (more specifically, left ventricle model and right ventricle model) and reproduces a fiber orientation based on the hypothesis is described in the present embodiment.

Figure 1:
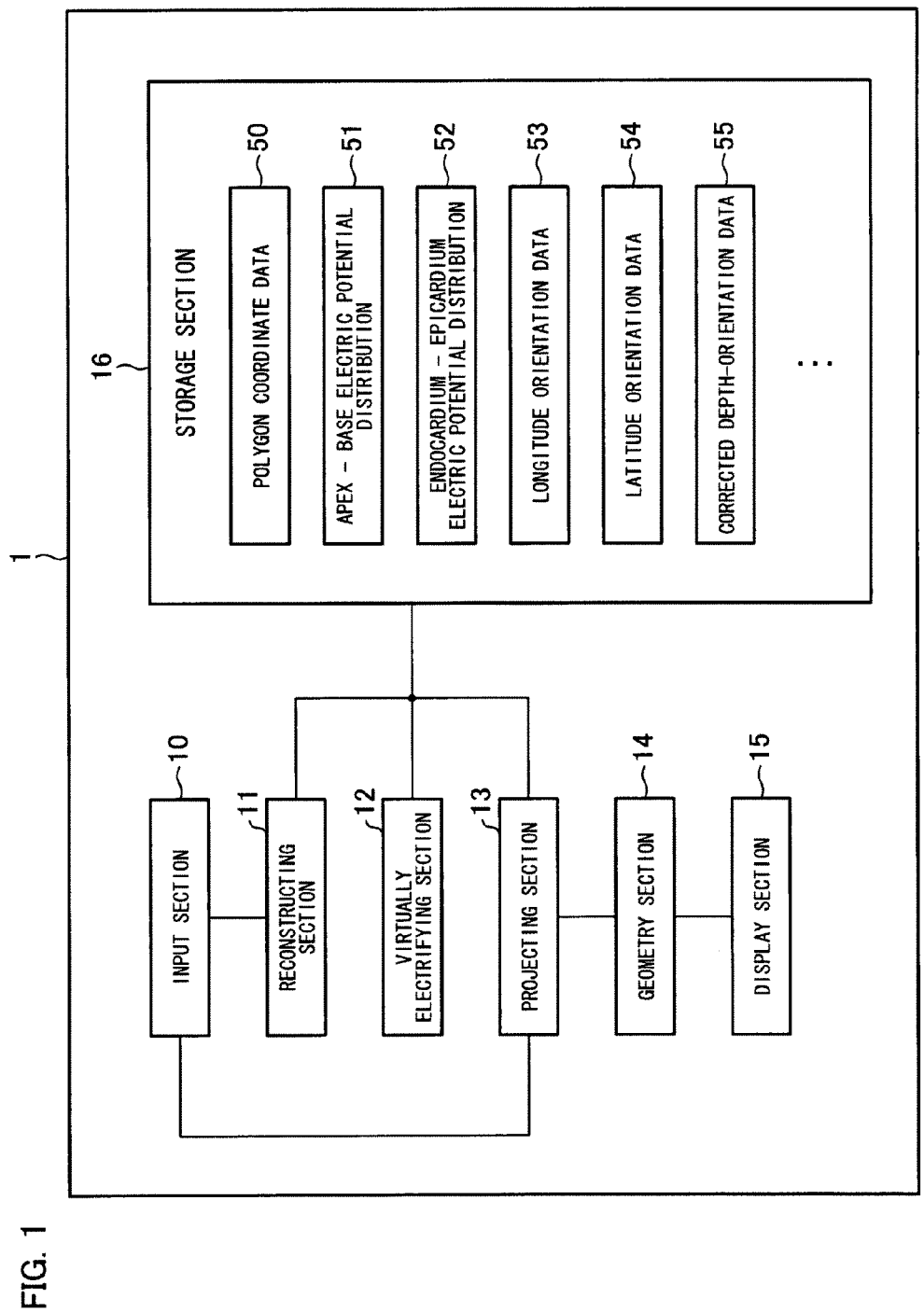
FIG. 1 This is a functional block diagram showing a configuration of a main part of a modeling device to illustrate an embodiment of the present invention.

FIG. 1 is a functional block diagram of a modeling device 1 of the present embodiment. The modeling device 1 includes an input section (first input section, second input section) 10, a reconstructing section 11, a virtually electrifying section (electrifying means, virtually electrifying means) 12, a projecting section (projecting means) 13, a geometry section (geometry means) 14, a display section 15, and a storage section 16.

Shape information on the human heart and a function indicating a relationship between a spot and a fiber orientation in the human heart are input into the input section 10. The input section 10 is not particularly limited. For example, a various data input interface which reads data from an external storage device, a keyboard with which a user inputs information by operating keys, or the like is used as the input section 10. The modeling device 1 may include a plurality of input sections, and the shape information and the function may be input into different input sections.

An example of the shape information of the human heart is a continuous tomography image taken with the use of X-ray CT (X-ray computed tomography) or MRI (magnetic resonance imaging). With these methods, the shape information on the heart is obtained in a non-invasive manner. Further, if obtained in advance, polygon coordinate data constituting the heart model may be utilized in place of the continuous tomography image. The function will be described concretely later.

The reconstructing section 11 reconstructs the heart model by converting the shape information on the human heart, which shape information is input to the input section, into the polygon coordinate data constituting the heart model. The reconstructing section 11 may be omitted in a case in which polygon coordinates are utilized as shape data of the human heart.

The virtually electrifying section 12 virtually applies a predetermined voltage to the human heart based on the shape information that is input to the input section 20, and obtains an electric potential and/or electric current orientation by calculation. Concretely, the virtually electrifying section 12 virtually applies a voltage to the heart model reconstructed three-dimensionally by the reconstructing section 11, and calculates the electric potential and the electric current orientation at respective spots in the heart model. In the present embodiment, the virtually electrifying section 12 virtually applies the voltage and calculates the electric potential and the electric current orientation by the method described below. Alternatively, an electrifying section (electrifying means) may be provided in place of the virtually electrifying section 12 so as to actually apply a voltage to a target object, such as a heart, and obtains the electric potential and the electric current orientation based on actually-measured values.

The projecting section 13 projects, onto the human heart model based on the shape information that is input to the input section, the fiber orientation contained in the function that is input to the input section. The fiber orientation is projected at a spot contained in the characteristic information. Concretely, the projecting section 13 projects the fiber orientation onto the human heart model reconstructed by the reconstructing section 11. To specify the spot at the time of projection, the projecting section 13 utilizes the electric potential obtained by the virtually electrifying section 12.

The geometry section 14 performs a geometry process on the human heart model on which the fiber orientation is projected by the projecting section 13. The geometry process is to convert a coordinate system defining the heart model from a modeling coordinate system to a visual coordinate system with a viewpoint being an origin of the visual coordinate system. The geometry process includes calculation of various effects such as perspective rules to perform conversion for projection, and conversion into a screen coordinate system so that the human heart model fits in a screen on which the human heart model is to be displayed.

The display section 15 displays images of the heart model on which the geometry process is performed by the geometry section 14. A CRT (cathode-ray tube), a liquid crystal display, or the like is employed as the display section 15.

The storage section 16 stores: coordinate data of the heart model reconstructed by the reconstructing section 11; and data of the electric potential and the electric current orientation at respective spots in the heart model, which electric potential and the electric current orientation are obtained by the virtually electrifying section. Specifically, the storage section 16 stores the following data described below: polygon coordinate data 50; apex—base electric potential distribution 51; endocardium—epicardium electric potential distribution 52; longitude orientation data 53; latitude orientation data 54; corrected depth data 55; and the like. The storage section 16 is constituted of various memories such as RAM (Random Access Memory).

The reconstructing section 11, the virtually electrifying section 12, the projecting section 13, and the geometry section 14 may be constituted solely of hardware such as dedicated IC, or may be constituted of a combination of hardware and software such as a combination of a CPU, a memory, and a program.

Figure 2:
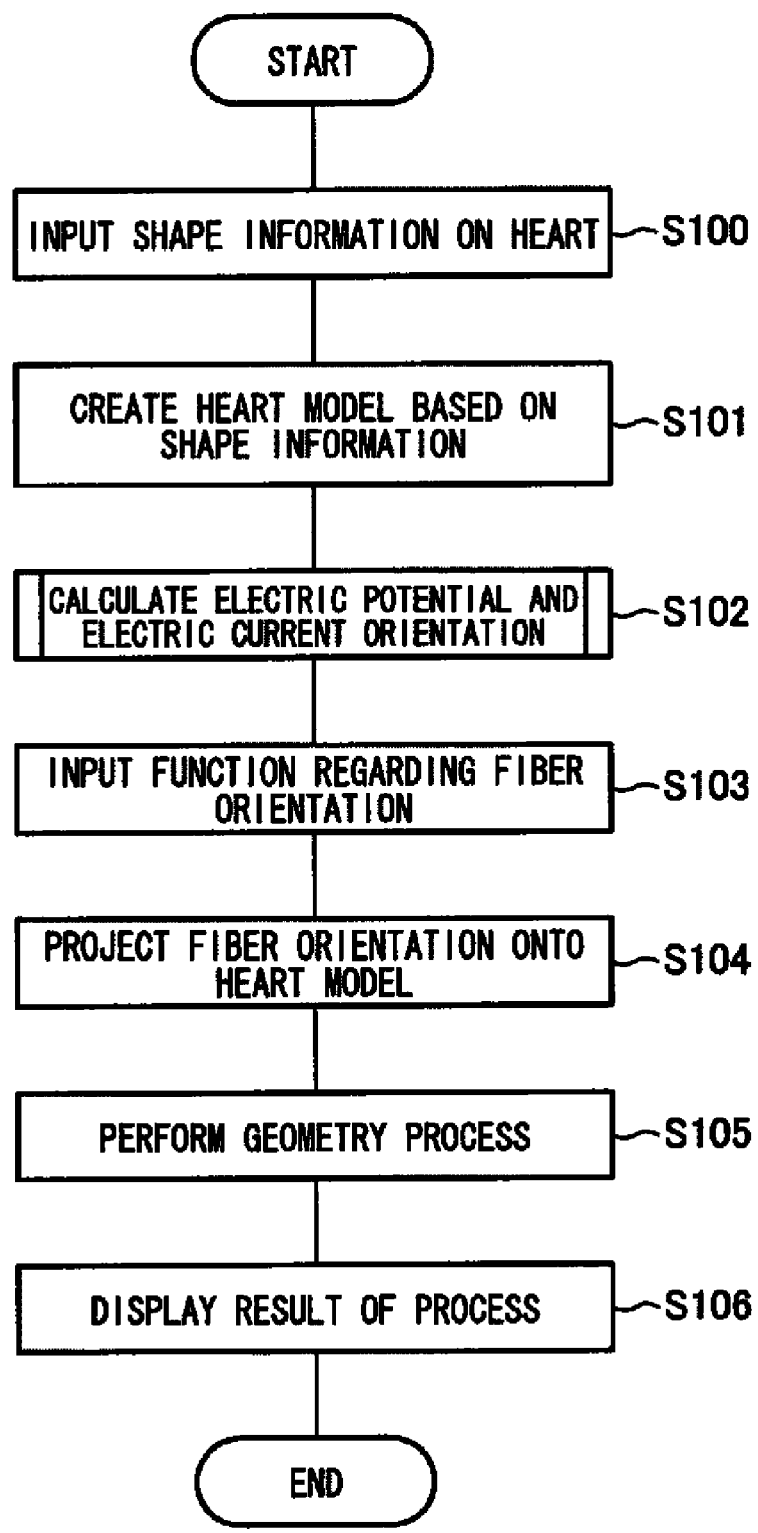
FIG. 2 This is a flowchart showing a process sequence of the modeling device shown in FIG. 1.

The following describes operation of the modeling device 1 of the present embodiment. FIG. 2 is a flowchart showing a process sequence of the modeling device 1.

First, the shape information on the human heart is input into the input section 10 of the modeling device 1 (step S100). In the present embodiment, an exemplary case is described in which the shape information to be input is a series of continuous tomography images taken with MRI. In this case, a heart image taken continuously along a line extending in vertical orientation of the heart (base—apex orientation) may be utilized as the continuous tomography images.

These input continuous tomography images are output to the reconstructing section 11. The reconstructing section 11 reconstructs the heart on the basis of the continuous tomography images to create the heart (more specifically, the left ventricle and the right ventricle) model (step S101). Specifically, when the continuous tomography images are input, the reconstructing section 11 performs image processing to extract borders (outlines) of endocardium and epicardium of the heart in respective tomography images. Then, correction of the outlines is performed on a part between one tomography image and the following tomography image. Consequently, a three-dimensional heart model is created on the basis of the continuous tomography image. Then, the reconstructing section 11 saves this obtained polygon coordinate data 50 of the heart model so that the polygon coordinate data 50 is stored in the storage section 16. Hereinafter, the coordinate system defining the polygon coordinate will be referred to as the modeling coordinate system. Step S101 may be omitted in a case in which the shape information input in step S100 is the polygon coordinate data.

The polygon coordinate data 50 stored in the storage section 16 is read out by the virtually electrifying section 12. The virtually electrifying section 12 virtually electrifies the heart model having read the coordinate data from the storage section 16, and calculates the electric potential and an orientation at respective spots in the heart model, in which orientation the electric current flows (the orientation will be referred to as "electric current orientation" hereinafter) (step S102).

Figure 3:
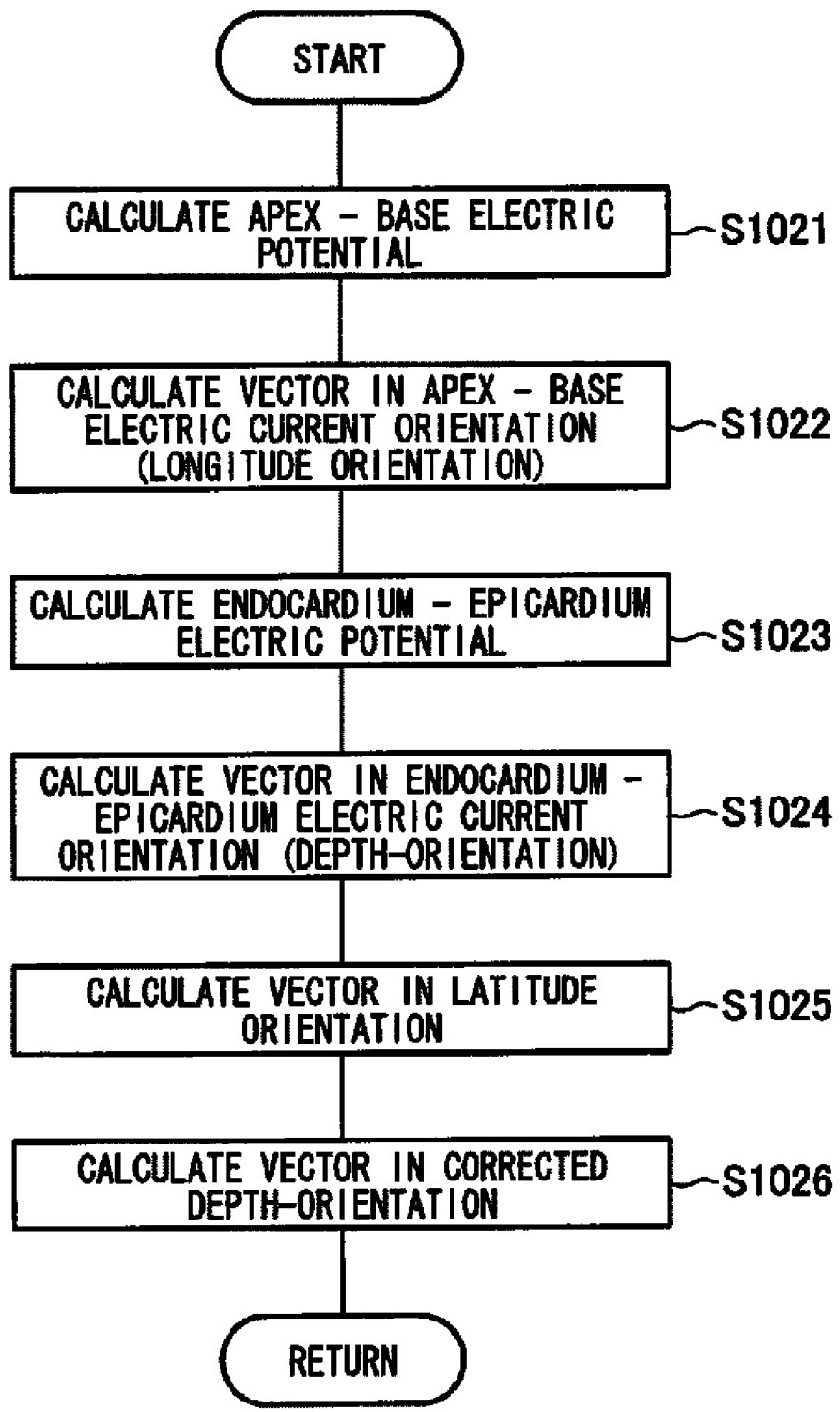
FIG. 3 This is a flowchart showing a process sequence of calculation in an electric-potential orientation and an electric current orientation, which process sequence is a part of the sequence shown in FIG. 2.
Figure 11:
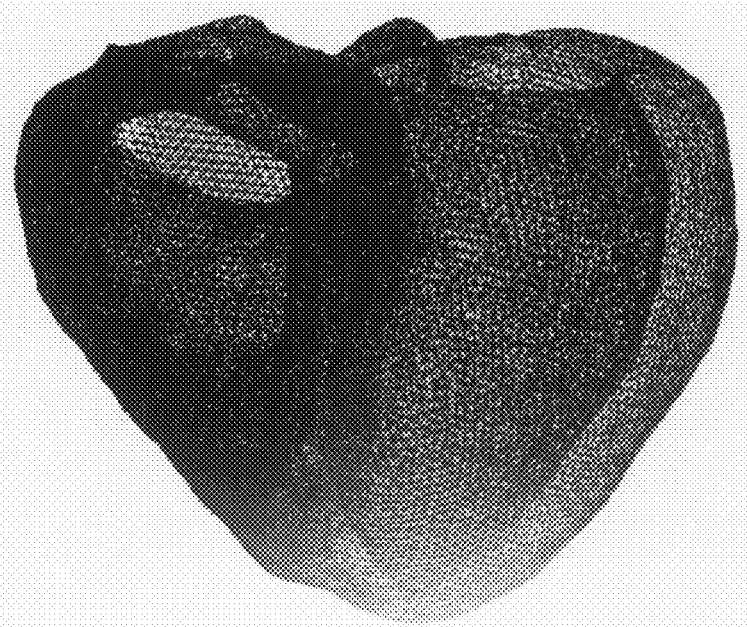
FIG. 11 This is a figure showing an apex—base electric potential distribution.

FIG. 3 shows details of step S102. First, the virtually electrifying section 12 virtually applies a voltage of 1V between an apex and a base of the heart model. In the present embodiment, the apex is a negative terminal, and the base is a positive terminal. Accordingly, the electric potential of the apex is 0V. The electric potential increases from the apex toward the base. The electric potential of the base is 1V. The virtually electrifying section 12 calculates an electric potential at respective spots in the heart model at the time when the voltage is applied between the apex and the base (the electric potential will be referred to as "apex—base electric potential" hereinafter) (step S 1021). A publicly-known method may be utilized to calculate the electric potential at a spot in the heart model. An exemplary method is solving the Poisson Equation by use of a finite element method. The electric potential may be calculated by use of market-available software such as MSC Nastran (registered trademark, manufactured by MSC software corporation). The virtually electrifying section 12 then saves this calculated apex—base electric potential distribution 51 so that the apex-base electric potential distribution 51 is stored in the storage section 16. The apex—base electric potential distribution 51, concretely, is correspondence information indicating a correspondence between the coordinate defined in the modeling coordinate system and the apex—base electric potential. For reference, a visualized calculated apex—base electric potential distribution 51 is shown in FIG. 11. As shown in this figure, the electric potential slops from the apex toward the base. The apex—base electric potential is utilized as one of the coordinates (electric potential coordinate) to specify a spot in the heart model. Although the exemplary case in which the virtually electrifying section 12 applies the voltage of 1V in the present embodiment, the voltage to be applied may be any voltage as long as it is a constant voltage.

Figure 4:
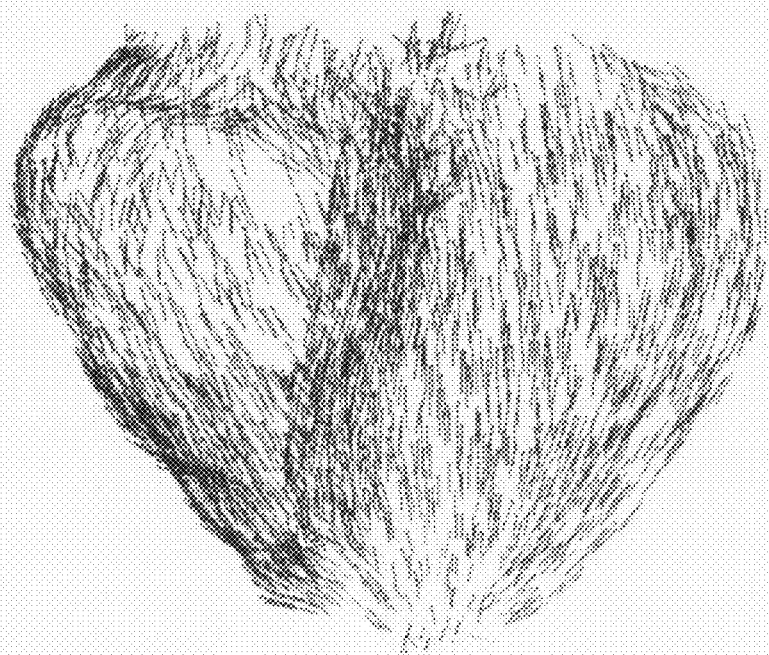
FIG. 4 This is a figure showing longitude orientation vectors calculated at respective spots.

Then, the virtually electrifying section 12 calculates, for respective spots in the heart, an orientation in which the electric current flows at the time when the voltage is applied between the apex and the base (the orientation will be referred to as "longitude orientation" hereinafter) (step S1022). The electric current flows in an orientation in which the electric potential slopes most steeply. Therefore, the longitude orientation is calculated by use of the electric potential distribution obtained in step S1021. The longitude orientation thus calculated is stored, as the longitude orientation data 53, into the storage section 16 by the virtually electrifying section 12. Specifically, components of vectors of the longitude orientation, which components are written in the modeling coordinate system, are stored in the storage section 16. FIG. 4 shows longitude orientation vectors calculated at respective spots. The longitude orientation is a first coordinate axis in a local coordinate system at respective spots in the heart model.

Figure 12:
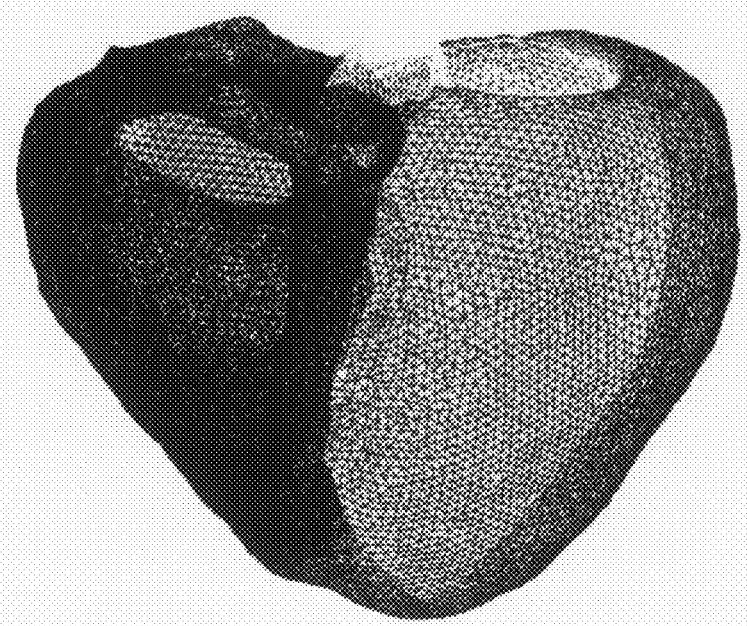
FIG. 12 This is a figure showing an endocardium—epicardium electric potential distribution.

Then, in the same manner as in step S1021, the virtually electrifying section 12 virtually applies the voltage of 1V between the endocardium and the epicardium of the heart model. The left ventricle model and the right ventricle model are employed as the heart model in the present embodiment, so that the same operation is performed on each of a left ventricle and a right ventricle. In the present embodiment, the endocardium is the negative terminal, and the epicardium is the positive terminal. Accordingly, the electric potential of the endocardium is 0. The electric potential increases from the endocardium toward the epicardium. The electric potential of the epicardium is 1V. The virtually electrifying section 12 calculates the electric potential at respective spots in the heart model at the time when the voltage is applied between the endocardium and the epicardium (the electric potential will be referred to as "endocardium—epicardium electric potential" hereinafter) (S1023). A visualized calculated endocardium—epicardium electric potential distribution 52 is shown in FIG. 12 as an example. As shown in this figure, the electric potential slops from the endocardium toward the epicardium. The endocardium—epicardium electric potential distribution 52 thus calculated for each of the spots is stored into the storage section 16 by the virtually electrifying section 12. The endocardium—epicardium electric potential distribution 52, concretely, is correspondence information indicating a correspondence between the coordinate defined in the modeling coordinate system and the endocardium—epicardium electric potential. The endocardium—epicardium electric potential is utilized as one of the coordinates to specify a spot in the heart model.

Figure 5:
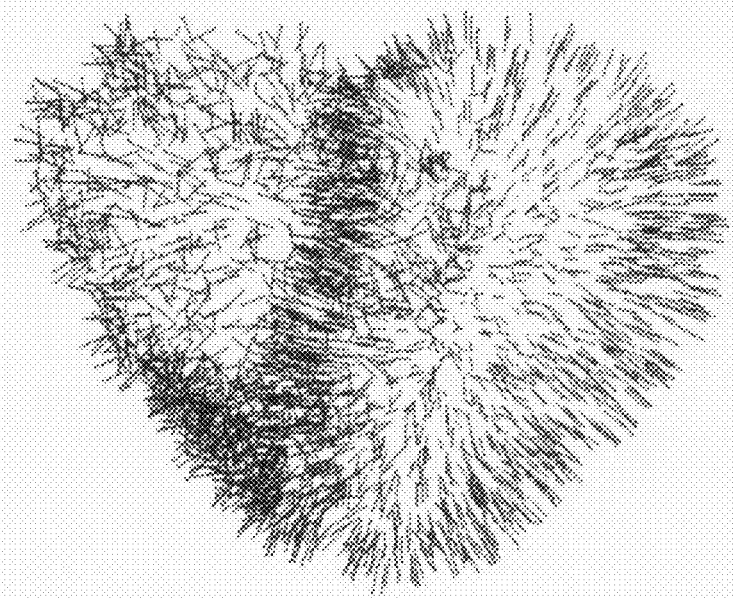
FIG. 5 This is a figure showing depth-orientation vectors calculated at respective spots.

Then, in the same manner as in step S1022, the virtually electrifying section 12 calculates, for each of the right ventricle and the left ventricle, an orientation in which the electric current flows at the time when the voltage is applied between the endocardium and the epicardium (the orientation will be referred to as "depth orientation" hereinafter) (step S1024). FIG. 5 shows depth-orientation vectors calculated for the left ventricle.

Figure 6:
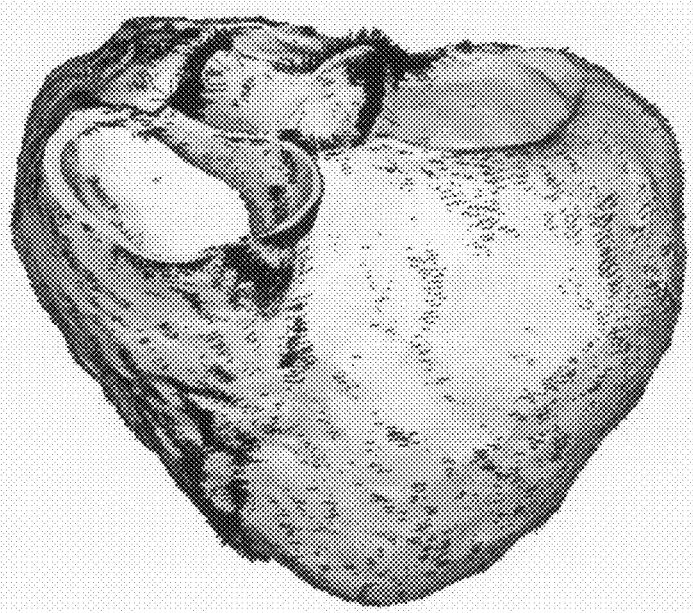
FIG. 6 This is a figure showing latitude orientation vectors calculated at respective spots.

Thereafter, the virtually electrifying section 12 calculates a cross product of the vector in the longitude orientation as shown in FIG. 4 and the vector in the depth orientation as shown in FIG. 5, thereby calculating, for respective spots in the heart, a vector orthogonal to either of the longitude orientation and the depth orientation (the vector will be referred to as "latitude-orientation vector" hereinafter) (step S1025). The latitude orientation thus calculated is stored, as the latitude orientation data 54, into the storage section 16 by the virtually electrifying section 12. The latitude orientation data 54, concretely, defines components of the latitude-orientation vector in the modeling coordinate system. FIG. 6 shows the latitude-orientation vector thus calculated. The latitude orientation is a second coordinate axis in the local coordinate system at respective spots in the heart model.

Consequently, those three orientations are obtained: the longitude orientation; the depth-orientation; and the latitude orientation. In some cases, the longitude orientation and the depth orientation are not perfectly orthogonal. It is thus necessary to correct the depth orientation so that the depth orientation becomes perfectly orthogonal to the longitude orientation. In other words, the virtually electrifying section 12 calculates a cross product of the vector in the longitude orientation and the vector in the latitude-orientation vector to calculate, for respective spots in the heart, a vector orthogonal to either of the longitude orientation and the latitude orientation (the vector will be referred to as "corrected depth-orientation vector" hereinafter) (step S1026). This corrected depth orientation is substantially equal to the depth orientation obtained in step S1024, but is perfectly orthogonal to either one of the longitude orientation and the latitude orientation. The corrected depth orientation thus calculated is stored, as the corrected depth orientation data 55, into the storage section 16 by the virtually electrifying section 12. The corrected depth orientation data 55, concretely, defines components of the corrected depth-orientation vector in the modeling coordinate system. The corrected depth orientation is a third coordinate axis in the local coordinate system at respective spots in the heart model. The foregoing describes calculation of the electric potential and the electric current orientation by the virtually electrifying section 12.

The fiber orientation at respective spots in the heart model are defined as angle components in the local coordinate system constituted of the longitude orientation, the latitude orientation, and the corrected depth-orientation. The modeling device 1 defines the fiber orientation by use of the local coordinate system, whereby the fiber orientation is defined in such a manner that a correspondence is established between the fiber orientation and an outer shape of the heart. This allows the fiber orientation to be projected onto the heart model in such a way as to fit in the outer shape of this target heart model.

Further, to specify a spot in the heart model, a rotation angle is set as the third coordinate, in addition to the apex—base electric potential and the endocardium—epicardium electric potential. The rotation angle is an angle in a rotation orientation having a central axis passing through the apex and the base. The rotation angle is defined with a characteristic spot in the heart being a base point. The characteristic spot only needs to be identifiable regardless of individuals or species and clearly distinguishable. In the present embodiment, an exemplary case is discussed in which a long axis in the orientation between the apex and the base of the left ventricle is a center, an orientation of a most protruded part of the right ventricle is 0°, and an anticlockwise orientation from the viewpoint of the base is a positive angle. The foregoing allows the modeling device 1 of the present embodiment to specify a spot on the object by the following three coordinates: the apex—base electric potential (0–1); the endocardium—epicardium electric potential (0–1); and the rotation angle (0–2π). Hereinafter, these coordinates will be referred to as electric potential coordinates, and this coordinate system will be referred to as an electric potential coordinate system. With this arrangement, spots in hearts of various shapes and sizes are specified by use of a common coordinate, which is the electric potential coordinate.

Then, the modeling device 1 requests an input of a function, which is a hypothesis regarding the fiber orientation. The function is supplied from the input section 10 as the characteristic information (step S103 in FIG. 2). The timing of the input of the function does not necessarily have to be after the virtually electrifying section calculates the electric potential and the electric current orientation. For example, the function may be input concurrently with inputting the shape information on the human heart.

Figure 7:
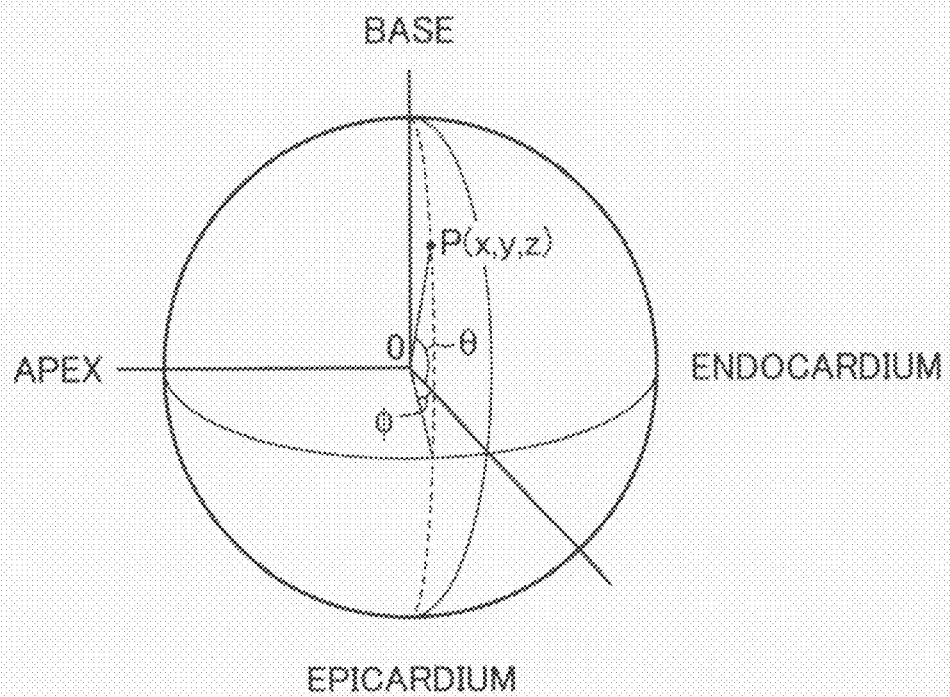
FIG. 7 This is a figure showing a local coordinate system to define a fiber orientation.
Figure 8:
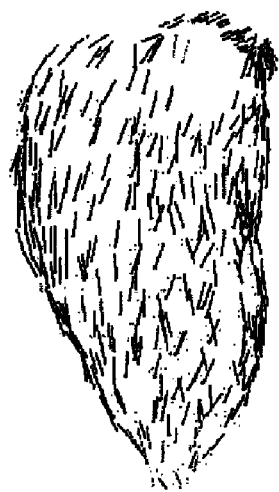
FIGS. 8(a) to 8(e) are figures each showing fiber placement reproduced on a human heart model by a modeling device of an embodiment of the present invention.
Figure 8:
Figure 8:
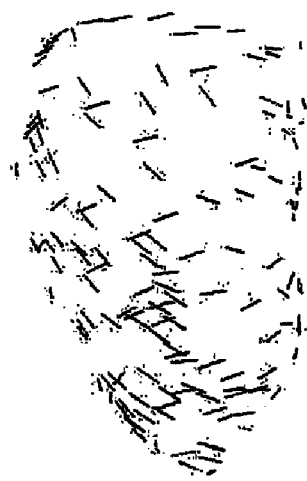
Figure 8:
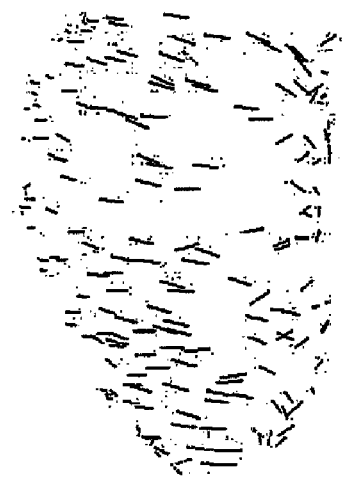
Figure 8:
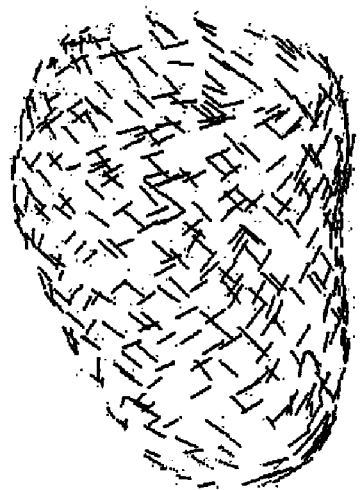

The following describes an exemplary function that is input. As shown in FIG. 7, the following are known in a case in which the fiber orientation is to be specified by angle components $\theta$, $\phi$ in the local coordinate system: the fiber orientation in the human heart is θ=−90° at the endocardium; the angle of the fiber orientation increases at shorter distances from the epicardium; the angle of the fiber orientation is θ=+60° at the epicardium; and φ is always 0°. This hypothesis is expressed by the following function $$\theta = -\pi/2 + 5\pi r/6$$

$$\phi = 0$$

$$(-\pi \leq \theta, \phi \leq \pi),$$

where r (0≦r≦1) is the coordinate of the corrected depth orientation.

The function thus input is then output to the projecting section 13. The projecting section 13 projects the fiber orientation expressed by the function onto the heart model (step S104). Specifically, the projecting section 13 performs the following operations. First, the projecting section 13 calculates θ and φ of an electric potential coordinate. Then, the projecting section 13 calculates, on the basis of the electric potential distributions 51, 52 stored into the storage section 16 in steps S1021, S1023, a modeling coordinate corresponding to the electric potential coordinate. The modeling coordinate is a target of projection on the heart model. Thereafter, components of the fiber orientation in the local coordinate system, which components are calculated as the angle components θ and φ, are converted into components in the modeling coordinate system by use of the orientation data 53, 54, 55 stored in the storage section 16 in steps S1022, S1025, S1026. Consequently, the fiber orientation in the electric potential coordinate is projected onto the heart model. The foregoing operations are repeated for a necessary number of times so that the fiber placement is reproduced on the heart model. The information on the heart model on which the fiber placement is reproduced is output to the geometry section 14.

The geometry section 14 performs the geometry process on the heart model on which the fiber placement is reproduced (step S105). Specifically, the geometry section 14 converts the coordinate system expressing the heart model from the modeling coordinate system to a visual coordinate system based on the viewpoint. The modeling coordinate system is a three-dimensional space. Conversion of the modeling coordinate system into the visual coordinate system that is two-dimensional plane makes it possible to represent the heart model on a plane. The coordinate data of the heart model, which coordinate data is converted into the visual coordinate system in the foregoing manner, is output to the display section 15. When receiving the coordinate data, the display section 15 displays, on the screen, the heart model on which the fiber placement is reproduced (step S106).

In the present embodiment, the fiber orientation of the cardiac muscle cell is projected. It is also possible to project a sheet orientation in the same manner.

EXAMPLE 1

A heart model to which the hypothesis is applied is shown in FIGS. 8(a) to 8(e) as an Example of the modeling device of Embodiment 1. FIGS. 8(a) to 8(e) indicate the fiber orientations at spots where the apex—base electric potential is 0V, 0.25V, 0.5V, 0.75V, and 1V, respectively. The figures show how the fiber orientation changes continuously from the endocardium toward the epicardium, changing from −90° to +60°. Further, the respective fiber orientations fit in the shape of the heart.

Embodiment 2

Figure 9:
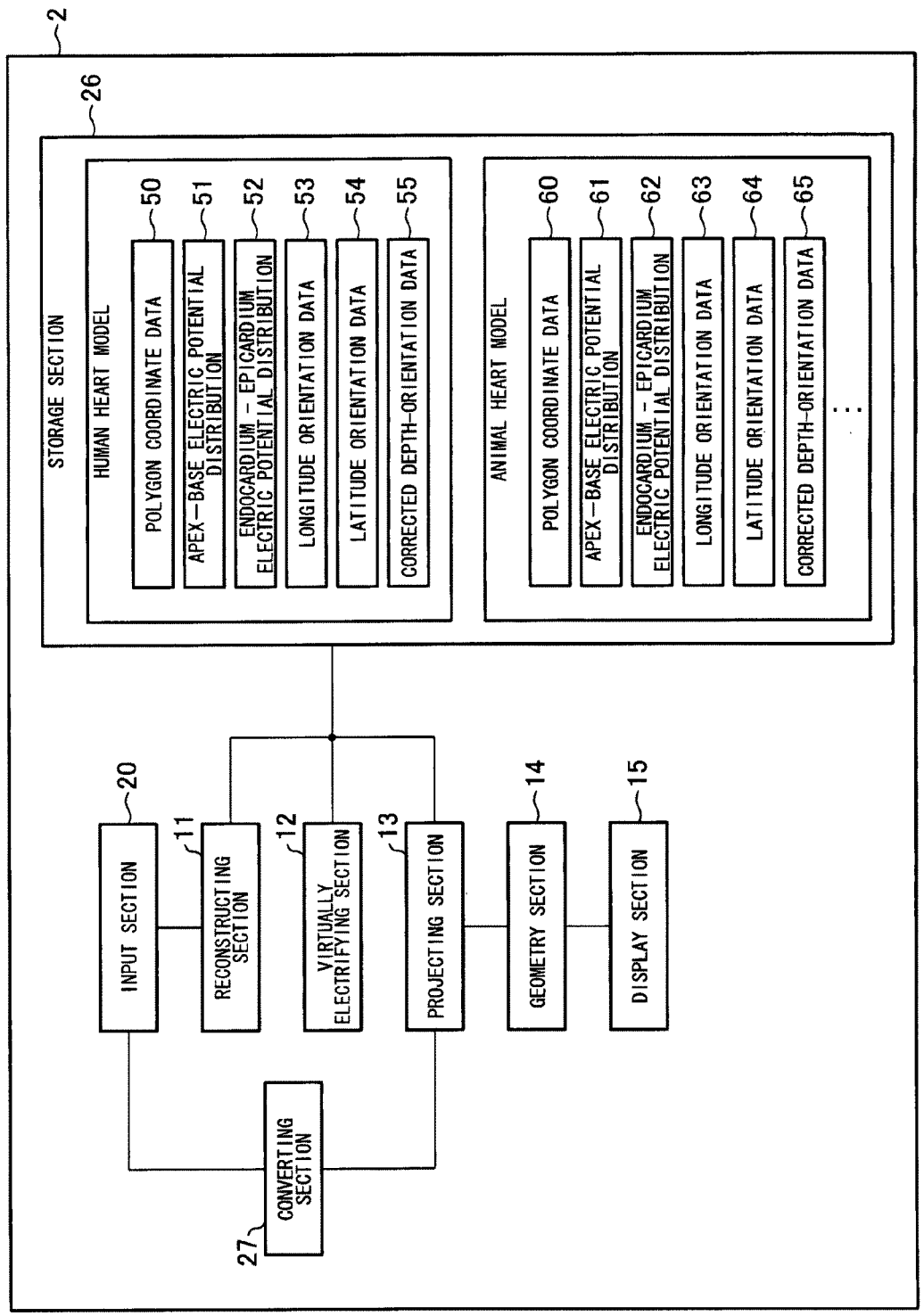
FIG. 9 This is a functional block diagram showing a configuration of a main part of a modeling device to show another embodiment of the present invention.
Figure 10:
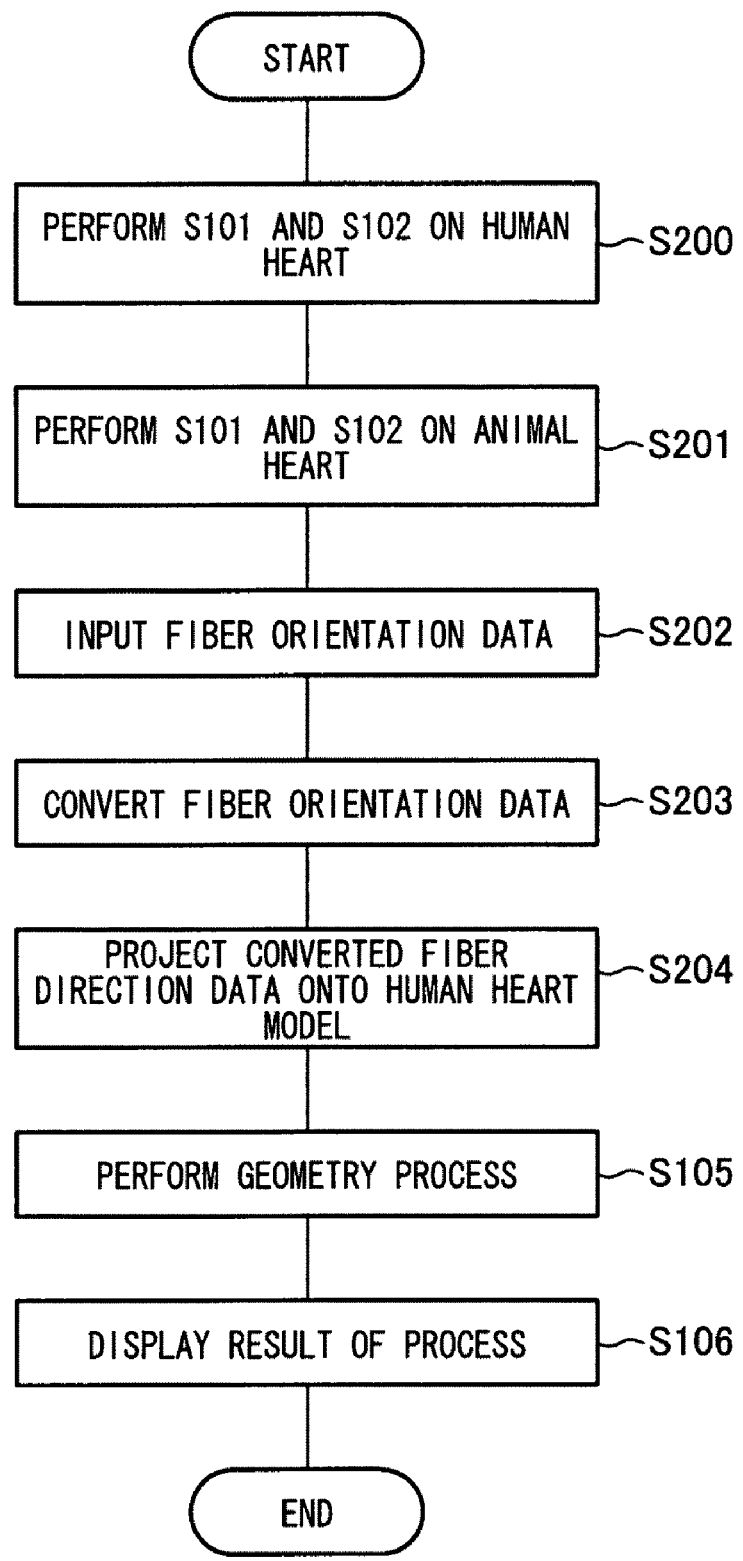
FIG. 10 This is a flowchart showing a process sequence of the modeling device shown in FIG. 9.

The following describes another embodiment of the present invention, with reference to FIGS. 9 and 10. In the present embodiment, a modeling device that projects fiber orientations of an animal heart onto a human heart model is described as an example. Components having equivalent functions as those of Embodiment 1 described above are given the same reference numerals, and description thereof is omitted.

FIG. 9 is a functional block diagram of a modeling device 2 of the present embodiment. The modeling device 2 includes an input section 20 (first input section, second input section, third input section) in place of an input section 10 of a modeling device 1 of Embodiment 1. Further, the modeling device 2 includes a storage section 26 in place of a storage section 16 of the modeling device 1 of Embodiment 1. Furthermore, the modeling device 2 includes a converting section (converting means) 27.

Shape information on a human heart (first object), shape information on an animal heart (second object), and fiber orientation information (characteristic information) on the animal heart are fed into the input section 20. Information same as the shape information on the human heart can be employed as the shape information on the animal heart. Further, fiber orientation information (hereinafter, "fiber orientation data") on the animal heart contains a combination of spot data to specify a spot on the animal heart and components of a vector indicating a fiber orientation at the spot. The spot data and the components of the vector are both defined in the modeling coordinate system.

The storage section 26 stores the following data on human: coordinate data of the heart model reconstructed by the reconstructing section 11; and data of the electric potential and the electric current orientation at respective spots in the heart model, which electric potential and the electric current orientation are calculated by the virtually electrifying section 12. The storage section 26 also stores the following data on animal: coordinate data of the heart model reconstructed by the reconstructing section 11; and data of the electric potential and the electric current orientation at respective spots in the heart model, which electric potential and the electric current orientation are calculated by the virtually electrifying section 12. Concretely, the storage section 26 stores the following data on a human heart: polygon coordinate data 50; an apex—base electric potential distribution 51; an endocardium—epicardium electric potential distribution 52; longitude orientation data 53; latitude orientation data 54; and corrected depth data 55. Further, the storage section 26 stores the following data on an animal heart: polygon coordinate data 60; an apex—base electric potential distribution 61; an endocardium—epicardium electric potential distribution 62; longitude orientation data 63; latitude orientation data 64; and corrected depth data 65. The storage section 26 is constituted of various memories such as RAM (Random Access Memory).

The converting section 27 converts a characteristic (fiber orientation) contained in the characteristic information input to the input section 20 into orientation data based on a local coordinate system of the second object (animal heart). Specifically, the converting section 27 converts fiber orientation information supplied via the input section 20 and defined in a modeling coordinate system so that the fiber orientation information is defined in a local coordinate system. Ways of conversion will be described in detail later. The converting section 27 may be constituted solely of hardware such as dedicated IC, or may be constituted of a combination of hardware and software such as a combination of a CPU, memory, and a program.

The following describes operation of the modeling device 2 of the present embodiment. FIG. 10 is a flowchart showing a process sequence of the modeling device 2. The processes same as those of Embodiment 1 described above are given the same reference numerals, and detailed description thereof is omitted.

First, the shape information on the human heart and the shape information on the animal heart are input into the input section 20 of the modeling device 2. The modeling device 2 carries out the processes of S101 and S102 with the use of the shape information (step S200) on the human heart. As a result, the following data on the human heart model are stored in the storage section 16: the polygon coordinate data 50; the electric potential distributions 51, 52; and the orientation data 53, 54, 55 on the local coordinate system.

Then, the processes of S101 and S102 are carried out on the animal heart in the same manner (step S201). As a result, the following data on the animal heart model are stored in the storage section 16: the polygon coordinate data 60; the electric potential distributions 61, 62; and the orientation data 63, 64, 65 on the local coordinate system.

Thereafter, the modeling device 2 requests an input of the fiber orientation data obtained from the animal heart. The fiber orientation data is input into the input section 10 as the characteristic information (step S202).

The fiber orientation data thus input is fed into the converting section 27. The converting section 27 converts this fiber orientation data defined in the modeling coordinate system so that the fiber orientation data is defined in the local coordinate system (step S203). The following concretely describes this conversion. The fiber orientation information is constituted of: spot data identifying a spot on the animal heart model; and the fiber orientation data of the spot. The spot data and the orientation data are both defined in the modeling coordinate system. The converting section 27 first refers to the orientation data 63, 64, 65 of the local coordinate system that are stored in the storage section 16, and calculates the local coordinate system at the spot specified by the spot data. Then, the converting section 27 converts the fiber orientation data defined in the modeling coordinate system into fiber orientation data defined in the local coordinate system by use of the vector components. Examples of the fiber orientation data in the local coordinate system are $\theta$ and $\phi$ in Embodiment 1. Consequently, the fiber orientation defined in the modeling coordinate system is converted into $\theta$ and $\phi$ in the local coordinate system. The fiber orientation data converted to the local coordinate system is input into the projecting section 13.

The projecting section 13 projects the animal fiber orientation data converted to the local coordinate system onto the human heart model (step S204). At this time, a correspondence between a spot in the animal heart model and a spot in the human heart model is established with the use of the electric potential coordinate. Specifically, the projecting section 13 projects the fiber orientation data at a spot in the animal heart model onto a spot in the human heart model, which spot in the human heart model has a same electric potential coordinate as the spot in the animal heart model. Further, the projecting section 13 converts, with the use of the orientation data 53, 54, 55 of the human local coordinate system, the fiber orientation data converted to the local coordinate system into the fiber orientation data defined in the modeling coordinate system. The projecting section 13 projects the fiber orientation data defined in the modeling coordinate system onto the human heart model.

The information on the heart model on which the fiber placement is reproduced by the projecting section 13 is supplied to the geometry section 14, and the geometry section 14 performs the geometry process (step S105). Then, the display section 15 displays, on the screen, the heart model on which the fiber placement is reproduced (step S106).

With the modeling device of the present embodiment, the correspondence is easily established between the spots on two heart models by use of the electric potential coordinate, even if the shapes of the hearts differ. Further, the fiber orientation data input is first converted into the local coordinate system and then projected onto the human heart model. This allows the fiber orientation to be suitably projected onto the heart models of various shapes.

The sections and the steps in the processes may be realized by the following arrangement. Calculation means, such as CPU, executes a program stored in storage means, such as ROM (Read Only Memory) and RAM, to control input means such as a keyboard, output means such as a display, and communication means such as an interface circuit. Accordingly, a computer having these means simply reads out the recording medium storing the program and executes the program to realize the functions and processes of the modeling device of the present embodiment. Further, storing the program in a removable recording medium allows the functions and the processes to be realized on any computer.

The recording medium may be a program media that is a memory (not illustrated), such as ROM, to perform the processes in a microcomputer. Alternatively, the recording medium may be a program media readable by inserting the recording medium into a program reading apparatus provided, although not illustrated, as an external storage apparatus.

In any of the cases, it is preferable that the program stored be accessed by the microprocessor to be executed. Further, it is preferable that the program be read out, the program thus read out be downloaded to a program storage area of a microcomputer and executed. The program to be downloaded is stored in advance in the main apparatus.

The program media is a recording medium that is removable from a main device and permanently holds programs. Examples of the program media include: tapes such as a magnetic tape and a cassette tape; disks such as a magnetic disk (e.g. flexible disk, hard disk) and CD/MO/MD/DVD; cards such as an IC card (including memory card); and semiconductor memories such as a mask ROM, an EPROM (Erasable Programmable Read Only Memory), an EEPROM (Electrically Erasable Programmable Read Only Memory), and a flash ROM.

Further, if the system allows a connection to a communication network, including the Internet, it is preferable that the recording medium temporarily hold the program by downloading the program from the communication network.

Further, if the program is to be downloaded from the communication network, it is preferable that the program to be downloaded be stored in advance in the main apparatus, or that the program be installed from another recording medium.

As the foregoing describes, the modeling device of the present invention includes: a first input section to which the shape information of the object is input; a second input section to which the characteristic information is input, which characteristic information contains the correspondence between the spot in the object and the characteristic; electrifying means for obtaining the electric potential at a spot in the object at the time when the predetermined voltage is applied to the object; and projecting means for projecting, onto the spot in the object model, the characteristic contained in the characteristic information that is input to the second input section, the spot being contained in the characteristic information, and the object model being based on the shape information that is input to the first input section. The projecting means specifies, on the basis of the electric potential obtained by the electrifying means, a spot that is a target of projection.

The characteristic information that is input to the second input section contains a correspondence between the spot in the object and the characteristic. The projecting means projects the characteristic information onto the object model that is input to the first input section. Thus, the characteristic corresponding to the spot is projected onto the object model. The "spot" may be either of a point and an area.

A spot in the object is specified on the basis of the electric potential obtained by the electrifying means. The electrifying means applies the predetermined voltage. Therefore, the electric potential at a spot in the object is in the range of 0V to the predetermined voltage. Accordingly, a spot in the object is specified in the range of 0V to the predetermined voltage. This makes it possible to specify the spot in various objects having different shapes by use of a common scale (not smaller than 0V and not greater than the predetermined voltage). Accordingly, for example a function with a variable of a coordinate based on the electric potential is input to the second input section as the characteristic information, the characteristic is easily projected regardless of shape of a target object. In other words, with the modeling device of the present invention, the characteristic is projected onto various objects having different shapes. Further, no geometric calculation is necessary to specify the spot, so that the characteristic is easily projected onto an object even if the object has a complex shape.

Further, it is preferable in the modeling device of the present invention that: the characteristic contained in the characteristic information be an orientation-related characteristic; the electrifying means obtain the electric current orientation at a spot in the object at a time when the voltage is applied to the object; and the projecting means project the orientation-related characteristic on the basis of the electric current orientation obtained by the electrifying means.

The orientation in which the electric current flows depends on the outer shape of the object. Hence, the electric current orientation can be utilized as the local coordinate system. The projecting means projects the orientation-related characteristic by use of the local coordinate system based on the electric current orientation. This makes it possible to project the orientation-related characteristic in such a way as to fit in the outer shape of the target object. Accordingly, with the modeling device of the present invention, the orientation-related characteristic related to the outer shape of the object is easily projected onto various objects of different shape.

Further, it is preferable in the modeling device of the present invention that: the electrifying means be virtually electrifying means for virtually applying the voltage to the object model based on the shape information that is input to the first input section, and obtaining the electric potential and/or the electric current orientation by calculation.

With this configuration, the electric potential and/or the electric current orientation at any spot in the object are obtained, even if a voltage cannot be actually applied to the object, such as a human heart.

Further, another modeling device of the present invention includes: a first input section to which the shape information of the first object is input; a second input section to which the characteristic information is input, which characteristic information contains a correspondence between the spot in the second object and the characteristic; electrifying means for obtaining the electric potential at a spot in the first object at a time when the predetermined voltage is applied to the first object and the electric potential at a spot in the second object at a time when the predetermined voltage is applied to the second object; and projecting means for (i) specifying, on the basis of the electric potential obtained by the electrifying means, a first spot in the fist object model based on the shape information that is input to the first input section, which first spot corresponds to a second spot in the second object, which second spot is contained in the characteristic information that is input to the second input section, and (ii) projecting the characteristic onto the spot.

With this configuration, the electrifying means applies the voltage to obtain the electric potential at a spot in the first object. In the same manner, the electrifying means obtains the electric potential at a spot in the second object. Then, the projecting means establishes a correspondence between the spot in the second object and the spot in the first object model on the basis of the electric potential at the spot in the second object. For example, the projecting means establishes a correspondence between the spot in the second object and the spot, having a same electric potential as that of the spot in the second object, in the first object model. Thereafter, the projecting means projects the characteristic information on the spot in the second object, which characteristic information is input to the second input section, onto the corresponding spot in the first object model. By the foregoing way, the characteristic information on a spot in the second object is projected onto the corresponding spot in the first object.

The projecting means establishes the correspondence between the spot in the first object and the spot in the second object on the basis of the electric potential obtained by the electrifying means. The electrifying means applies the predetermined voltage. Therefore, the electric potential at a spot in the objects is in the range of 0V to the predetermined voltage. Accordingly, a spot in each of the objects is specified in the range of 0V to the predetermined voltage. This makes it possible to easily establish a correspondence by use of a common scale (not smaller than 0V and not greater than the predetermined voltage) even if the shape of the first object and the shape of the second object are complex and different. Accordingly, with the modeling device of the present invention, a modeling device by which characteristic information obtained from an object is easily projected onto a differently-shaped object, even if the object, from which the characteristic information is obtained, has a complex shape. Further, no geometric calculation is necessary to establish a correspondence between spots, so that the characteristic is easily projected even if the object has a complex shape.

Further, it is preferable in the modeling device of the present invention that: the characteristic contained in the characteristic information relate to an orientation; and the electrifying means obtains, on the basis of the electric current orientation at a spot in the object at a time when the voltage is applied to the first object and at a time when the voltage is applied to the second object, the local coordinate system of the first object and the local coordinate system of the second object. Further, it is preferable that: the modeling device of the present invention further include converting means for converting the orientation-related characteristic contained in the characteristic information that is input to the second input section, into orientation data in the local coordinate system of the second object; and the projecting means project, on the basis of the local coordinate system of the first object, the orientation data converted by the converting means.

The orientation in which the electric current flows depends on the outer shape of the object. Hence, the electric current orientation can be utilized as the local coordinate system. The converting means converts the orientation-related characteristic input into an expression based on the local coordinate system. The projecting means projects the orientation-related characteristic expressed on the basis of the local coordinate system, so that orientation-related characteristic is projected in such a way as to fit in the outer shape of the target. This makes it possible to project the orientation-related characteristic onto the first object in such a way as to fit in the outer shape of the first object, even if the outer shape of the first object is different from that of the second object. Accordingly, with the modeling device of the present invention, the orientation-related characteristic related to the shape of the object is easily projected from an object onto another object.

Further, it is preferable that; the modeling device of the present invention further include a third input section to which the shape information of the second object is input; the electrifying means be virtually electrifying means for virtually applying the voltage to the object model based on the shape information that is input to the first input section and the object model based on the shape information that is input to the third input section, and obtaining the electric potential and/or the electric current orientation by calculation.

With this configuration, the electric potential and/or the electric current orientation at any spot in the object are obtained, even if a voltage cannot be actually applied to the object, such as a human heart.

Further, in the modeling device of the present invention, the object may be a heart, and the characteristic contained in the characteristic information that is input to the second input section may relate to the fiber orientation or the sheet orientation of a cardiac muscle cell.

With this configuration, the information on the fiber orientation or the sheet orientation of the cardiac muscle cell obtained from a heart is projected onto a target heart model. This makes it possible to realize a modeling device by which the information on the fiber orientation and the sheet orientation is projected onto a target heart model on the basis of findings of the fiber orientation or the sheet orientation from another heart, thereby contributing to medical treatment and diagnosis.

Further, it is preferable in the modeling device of the present invention that: the electrifying means obtain an electric potential at a spot in the heart at a time when the predetermined voltage is applied between the apex and the base and an electric potential at a spot in the heart at a time when the predetermined voltage is applied between the endocardium and the epicardium; the projecting means project the orientation-related characteristic as the characteristic information on the basis of (i) the electric potential at the time when the predetermined voltage is applied between the apex and the base, (ii) the electric potential at the time when the voltage is applied between the endocardium and the epicardium, and (iii) an angle along a rotation orientation having a central axis extending in an orientation between the apex and the base.

With this configuration, the spot in an orientation substantially corresponding to a height orientation of the heart is specified by the electric potential in the orientation between the apex and the base. Further, the spot in an orientation substantially corresponding to the depth orientation of the heart is specified by the electric potential in the orientation between the endocardium and the epicardium. Further, the spot in the rotation orientation is specified by the angle along the rotation orientation having the central axis extending in the orientation between the apex and the base. A coordinate system expressed by these three coordinates is similar to a cylindrical coordinate system or a spherical coordinate system, and can define any point in a three-dimensional space. Further, the coordinates of the coordinate system fit in the characteristic of the shape of the heart (i.e. a hollow spherical complex shape in which only an angle in a vertical orientation and an angle in the rotation orientation are easily identifiable), and therefore are suitable to specify a spot in the heart. Thus, a general specification of spots can be performed in a manner independent from differences in shape between species or individuals.

Further, it is preferable in the modeling device of the present invention that: the local coordinate system be an orthogonal coordinate system; a first coordinate axis of the local coordinate system extend in the electric current orientation at the time when the voltage is applied between the apex and the base; a second coordinate axis of the local coordinate system be orthogonal to the first coordinate axis and an axis extending in the electric current orientation at the time when the voltage is applied between the endocardium and the epicardium; and a third coordinate axis of the local coordinate system be orthogonal to the first coordinate axis and to the second coordinate axis.

When the voltage is applied between the apex and the base, the electric current orientation (i.e. orientation in which the first coordinate axis extends) is along a cardiac wall. Further, when the voltage is applied between the endocardium and the epicardium, the electric current orientation is substantially vertical to the cardiac wall. The second axis is vertical to the electric current and therefore is substantially along the cardiac wall. Further, the third axis is orthogonal to both of the first axis and the second axis and therefore is substantially vertical to the cardiac wall. Accordingly, the respective coordinates of the local coordinate system are related to the outer shape of the heart. This makes it possible to project information on the fiber orientation and the sheet orientation, both of which are related to the outer shape of the heart, in such a way as to fit in the shape of the target heart without contradiction.

Further, it is preferable that the modeling device of the present invention further include: geometry means for performing the geometry process on the object on which the characteristic is projected by the projecting means; and a display section to display the object on which the geometry process is performed by the geometry means.

With this configuration, the target object on which the characteristic information is projected is visually confirmed on the display section.

Respective means of the modeling device may be realized by hardware, or may be realized by causing a computer to execute a program. Concretely, a program of the present invention is to cause a computer to operate as any of the respective means of the modeling device. Further, a recording medium of the present invention stores the program.

If the program is executed by the computer, the computer operates as the respective means of the modeling device. Accordingly, a modeling device is realized by which characteristic information obtained from an object is easily projected onto a differently-shaped object, even if the object, from which the characteristic information is obtained, has a complex shape.

Further, a method of establishing a correspondence between a spot in a first object and a spot in a second object according to the present invention includes: obtaining an electric potential distribution at a time when the predetermined voltage is applied to the first object and an electric potential distribution at a time when the predetermined voltage is applied to the second object; and establishing, on the basis of the electric potential distribution thus obtained, a correspondence between the spot in the first object and the spot in the second object.

With this arrangement, the correspondence between the points or areas in the objects is established on the basis of the electric potential distribution. The electric potential distribution is a distribution at a time when the predetermined voltage is applied. Therefore, any spot in the objects is in the range of 0V to the predetermined voltage. Accordingly, any spot in the objects is specified in the range of 0V to the predetermined voltage. The foregoing arrangement makes it possible to establish a correspondence between the points or areas by use of a common scale (not smaller than 0V and not greater than predetermined voltage), even if the shapes of the first object and the second object are different.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

A modeling device of the present invention easily projects characteristic information obtained from an object onto a differently-shaped object, even if the object, from which the characteristic information is obtained, has a complex shape. Therefore, for example on the basis of findings obtained from an animal heart, a fiber orientation is projected onto a human heart to create a human heart model. The heart model may be utilized in medical care to give an explanation to a patient. Further, a simulation device to simulate heart beats is realized by applying the modeling device to the simulation device.

The invention claimed is:

1. A modeling device, comprising:
an input section configured to receive shape information on an object, and characteristic information,
the characteristic information indicating a correspondence between a spot in the object and a characteristic;
a processor; and
a storage unit storing executable code capable of causing the processor to implement a
virtually electrifying section configured to obtain by calculation, on a basis of the shape information that is input to the first input section, an electric potential at a spot in the object at a time when a predetermined voltage is applied to the object, and
a projecting section configured to project, onto an object model based on the shape information, the characteristic contained in the characteristic information,
the projecting section being configured to specify a spot in the object model on a basis of the electric potential obtained by the virtually electrifying means, onto which spot the characteristic is to be projected,
wherein the object is a heart and the characteristic includes a fiber orientation and/or a sheet orientation of a cardiac muscle cell.

2. The modeling device of claim 1, wherein:
the characteristic contained in the characteristic information is an orientation-related characteristic;
the virtually electrifying section is configured to obtain by calculation an electric current orientation at a spot in the object at a time when the voltage is applied to the object, and sets a local coordinate system of the object on a basis of the electric current orientation obtained; and
the projecting section is configured to project the orientation-related characteristic on a basis of the local coordinate system set by the virtually electrifying section.

3. The modeling device of claim 1, wherein:
the virtually electrifying section is configured to obtain (i) the electric potential at a spot in the heart at a time when the predetermined voltage is applied between an apex and a base and (ii) the electric potential at the spot in the heart at a time when the predetermined voltage is applied between an endocardium and an epicardium; and
the projecting section is configured to specify, on a basis of (i) the electric potential at the time when the predetermined voltage is applied between the apex and the base, (ii) the electric potential at the time when the voltage is applied between the endocardium and the epicardium, and (iii) an angle along a rotation orientation having a central axis extending in an orientation between the apex and the base, the spot in the object model, onto which spot the characteristic is to be projected.

4. The modeling device of claim 3, wherein:
the local coordinate system is an orthogonal coordinate system;
a first coordinate axis of the local coordinate system extends in the electric current orientation at a time when the voltage is applied between the apex and the base;
a second coordinate axis of the local coordinate system is orthogonal to either of the first coordinate axis and an axis extending in the electric current orientation at a time when the voltage is applied between the endocardium and the epicardium; and
a third coordinate axis of the local coordinate system is orthogonal to either of the first coordinate axis and the second coordinate axis.

5. The modeling device of claim 1, wherein the storage unit further stores executable code capable of causing the processor to implement a
geometry section configured to perform a geometry process on the object model on which the characteristic is projected by the projecting means; and
a display section configured to display the object model on which the geometry process is performed by the geometry means.

6. A non-transitory computer readable medium storing a program, the program including code executable by a computer to cause the computer to implement the input section, virtually electrifying section, and projecting section of the modeling device of claim 1.

* * * * *